(12) United States Patent
Masalin (10) Patent No.: US 12,274,602 B2
(45) Date of Patent: Apr. 15, 2025

(54) EAR PROTECTION DEVICE (71) Applicant: Fiskars Finland Oy Ab, Espoo (FI)

(72) Inventor: Petteri Masalin, Espoo (FI)

(73) Assignee: Fiskars Finland Oy Ab, Espoo (FI)

( * ) Notice: Subject to any disclaimer, the term of this patent is extended or adjusted under 35 U.S.C. 154(b) by 384 days.

(21) Appl. No.: 17/732,664

(22) Filed: Apr. 29, 2022

(65) Prior Publication Data
US 2022/0354699 A1 Nov. 10, 2022

(30) Foreign Application Priority Data

May 5, 2021 (FI) ...................................... 20215523

(51) Int. Cl.
A61F 11/14 (2006.01)
A61F 11/06 (2006.01)
A61F 11/12 (2006.01)

(52) U.S. Cl.
CPC .............. A61F 11/14 (2013.01); A61F 11/06 (2013.01); A61F 11/12 (2013.01)

(58) Field of Classification Search
CPC .................................. A61F 11/06; A61F 11/14
See application file for complete search history.

(56) References Cited

U.S. PATENT DOCUMENTS

| 8,718,312 B2* | 5/2014 | Lin | H04R 1/1008 |
| | | | 181/129 |
| 8,873,791 B2* | 10/2014 | Yang | H04R 1/1075 |
| | | | 381/372 |
| 8,897,478 B2* | 11/2014 | Yang | H04R 1/1041 |
| | | | 381/372 |
| 10,165,348 B2* | 12/2018 | Kirsch | H04R 3/04 |
| 2002/0146142 A1 | 10/2002 | Myers | |
| 2004/0125976 A1* | 7/2004 | Reneker | H04R 1/1041 |
| | | | 381/372 |
| 2005/0105755 A1* | 5/2005 | Yueh | H04R 1/1041 |
| | | | 381/370 |

(Continued)

FOREIGN PATENT DOCUMENTS

| CA | 2631087 | 11/2009 |
| WO | WO-96/23462 | 8/1996 |

OTHER PUBLICATIONS

Search Report for Finnish Patent Application No. 20215523, dated Nov. 22, 2021, 2 pages.

Primary Examiner — Keri J Nelson
(74) Attorney, Agent, or Firm — FOLEY & LARDNER LLP (57) ABSTRACT The present invention relates to an ear protection device, which comprises an ear cushion for contacting around an ear to seal off an interior space of the ear protection device from surroundings, a switch comprising a holder portion and a shaft with a guide, a shell comprising an interior section and a shell aperture wherein edges of the shell aperture engage with the guide of the switch, and said shell is provided between the ear cushion and the switch. The switch is rotatable between a first position and a second position, wherein in the first position ventilation holes are exposed from the interior section of the shell allowing air to flow inside the interior space, and in the second position the ventilation holes are covered inside the interior section of shell preventing the air to flow inside the interior space.

20 Claims, 6 Drawing Sheets (56) References Cited

U.S. PATENT DOCUMENTS

| | | | |
|---|---|---|---|
| 2009/0232340 A1* | 9/2009 | Yang | .................... H04R 1/2811 |
| | | | 381/371 |
| 2012/0207320 A1 | 8/2012 | Avital | |
| 2015/0036834 A1 | 2/2015 | Bauman et al. | |
| 2016/0199228 A1 | 7/2016 | Haukap | |
| 2019/0380877 A1* | 12/2019 | Werner | ................... A61F 11/14 |

* cited by examiner

EAR PROTECTION DEVICE

CROSS-REFERENCE TO RELATED PATENT APPLICATIONS

This Application claims the benefit of priority to Finland patent application number 20215523, filed on May 5, 2021, the complete disclosure of which is hereby incorporated by reference for all purposes.

TECHNICAL FIELD

The present invention relates to an ear protection device, and more particularly to a noise attenuator with a switch.

BACKGROUND

Ear protection devices are widely used in construction sites, logging industry, army, etc. to protect ears from loud noises which might damage hearing or, in worst case, cause loss of hearing completely. It is one of the most important occupational health concerns and in many workplaces wearing the ear protection device is mandatory, when the daily noise exposure exceeds 80 decibels (dB).

For effective and reliable hearing protection, ear protection devices are tested to meet regulations set in standards. For instance, European Standards (EN) has hearing protection standard EN352, and all ear protection products marketed in Europe must meet the EN352 series. Only the products which have been tested and met the regulations can receive EN352 certification.

Every hearing protection product will come with a Single Number Rating (SNR), which allows the user to compare the protection offered by different products. The higher the SNR level, the more protection the product gives.

One of the disadvantages associated with the ear protection devices is that sometimes users need to communicate with each other when the surrounding loud noises, such as from machines, are turned off, and it is impossible to switch the attenuation off without taking the ear protection device off. Additionally, effective ear protection devices allow no ventilation to the ears, and therefore the user's ear area becomes sweaty and uncomfortable after hours of use. In order to have some comfort or allow the user to communicate, the user would take the ear protection device off and there's a chance the user might misplace it.

BRIEF DESCRIPTION

It is thus an object of the present invention to provide an ear protection device to alleviate the above disadvantages without taking the ear protection device off. The objects of the invention are achieved by a device which is characterized by what is stated in the independent claim. The preferred embodiments of the invention are disclosed in the dependent claims.

The invention is based on the idea of a rotatable switch. At a first position, ventilation is allowed, and attenuation is off. At a second position, ventilation is closed, and attenuation is on.

BRIEF DESCRIPTION OF THE DRAWINGS

In the following the invention will be described in greater detail by means of preferred embodiments with reference to the accompanying drawings, in which.

DETAILED DESCRIPTION

Figure 1:
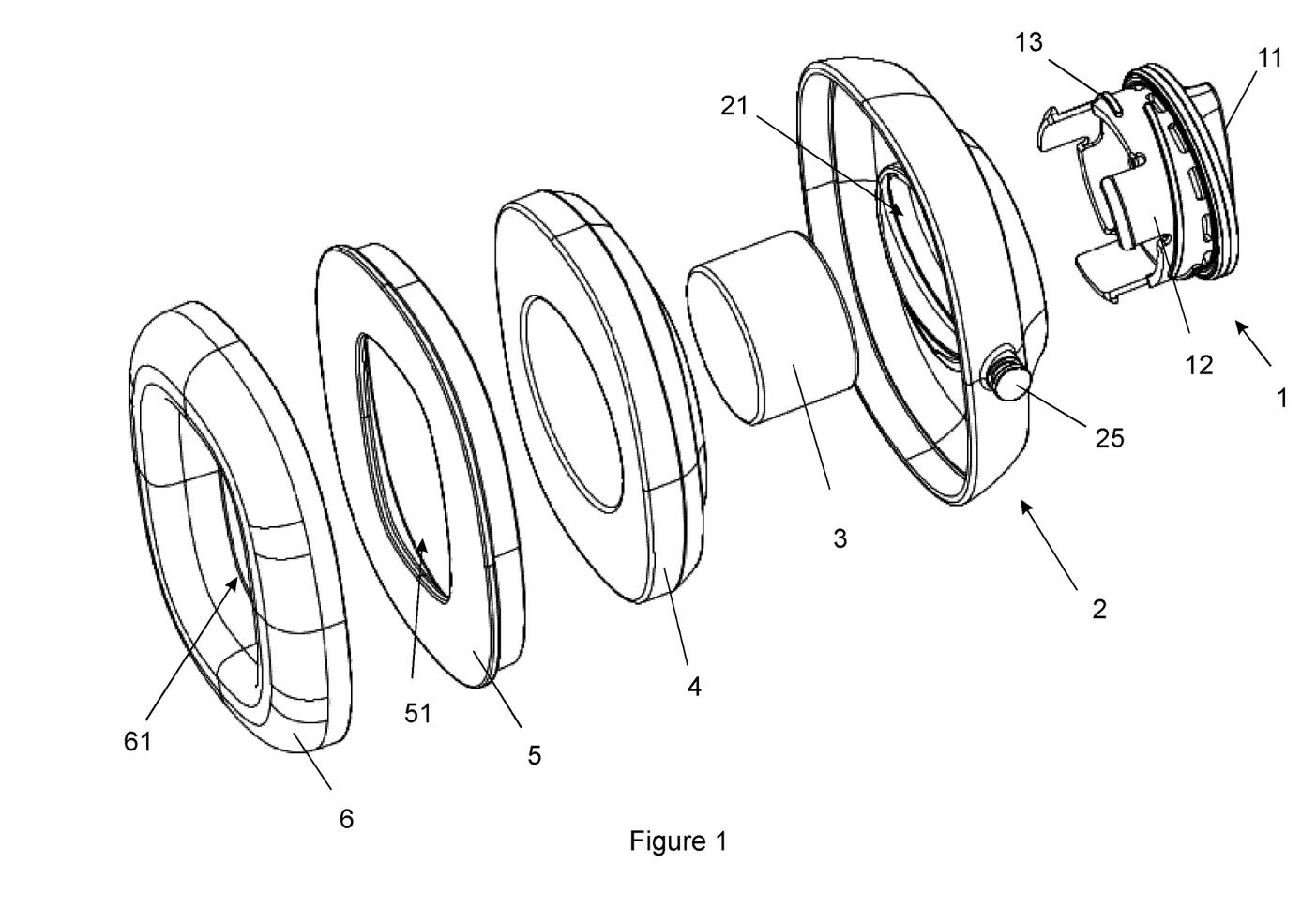
FIG. 1 illustrates an exploded view of an ear protection device according to a first embodiment.
Figure 2:
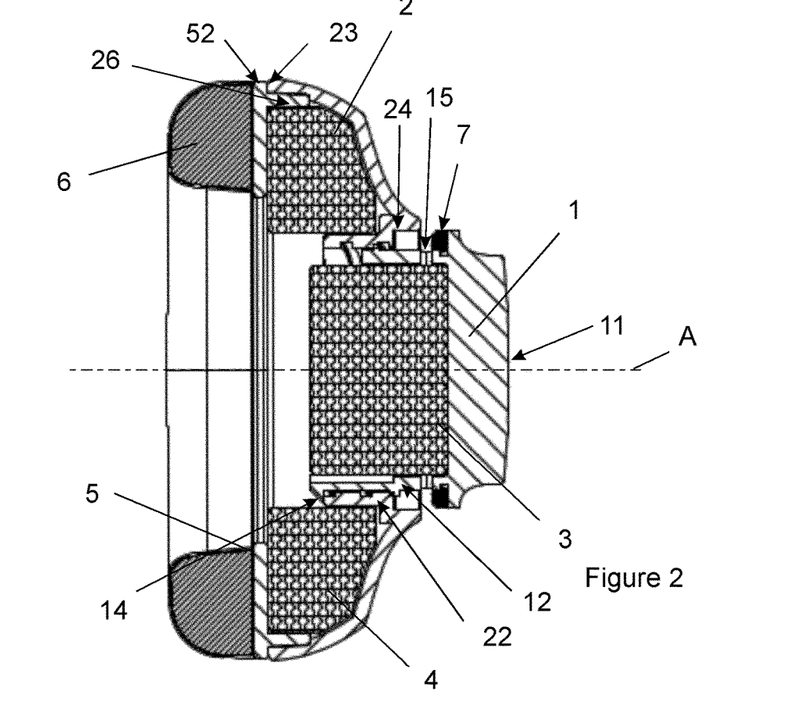
FIG. 2 illustrates a cross-sectional view of the ear protection device according to the first embodiment in the first position.
Figure 3:
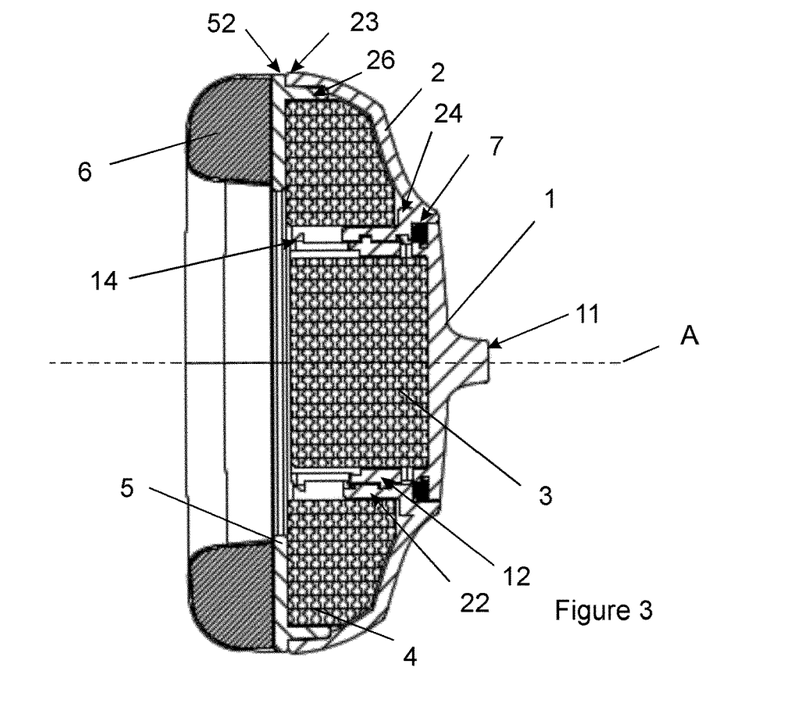
FIG. 3 illustrates a cross-sectional view of the ear protection device according to the first embodiment in a second position.

FIGS. 1-4 illustrate an ear protection device according to a first embodiment. FIG. 1 illustrates an exploded view of the ear protection device. FIG. 2 illustrates a cross-sectional view of the ear protection device according to the first embodiment in the first position, and FIG. 3 illustrates a cross-sectional view of the ear protection device according to the first embodiment in a second position. The ear protection device comprises an ear cushion 6, at least one sound-absorbing element 3, 4, a shell 2 and a rotatable switch 1, wherein the switch 1 is rotatable in relation to the shell 2 and the ear cushion 6.

The ear cushion 6 is for contacting a user around the user's ear to seal off an interior space from surroundings. The ear cushion 6 also provides comfort to the user as usually such cushions are made of soft foam. The outline of the ear cushion 6 may be circular or oval or rounded rectangle shape and having an ear cushion aperture 61 forming at least part of the interior space for the ear. The interior space is defined by interior sections of the ear protection device. When the ear protection device is in use, the ear cushion 6 presses against the skin of the user and is configured to attenuate surrounding noises to lower and more harmless level.

The rotatable switch 1 comprises a holder portion 11 to which the user can hold with fingers. The holder portion 11 can be a protrusion from one end of the switch 1, and it can be flat or rounded knob. In the accompanying Figures, the holder portion 11 is illustrated as a flange extending outward from an exterior surface of the switch 1.

The switch 1 additionally comprises a shaft 12 extending to the other end of the switch 1 which is opposite to the holder portion 11. The shaft 12 is arranged to fit inside an aperture 21 of the shell 2. The shaft 12 may comprise a guide 13. The guide 13 in this context can refer to any mechanism engaging with the edges of the shell aperture 21, such as a protrusion or a clamp. In the accompanying FIGS. 1-4, the guide 13 is illustrated as threads around outer surface of the shaft 12.

The ear protection device may also comprise an intermediate shell 5 between the shell 2 and the ear cushion 6, and the intermediate shell 5 having an intermediate shell aperture 51. The inner surface of the shell 2 and the inner surface of the intermediate shell 5 and optionally the outer surface of the shaft 12 of the switch 1 defines a space for a main sound-absorbing element 4, which can be made of a material such as foam. The main sound absorbing element 4 is configured to attenuate surrounding noises to lower and more harmless level. Having a separate intermediate shell 5 may reduce production time, where the ear protection device may be manufactured by stacking the parts on top of each other. However, in some embodiments, the intermediate shell 5 may be integrated as part of the shell 2.

As illustrated in the FIGS. 1-3, the shell 2 has an interior section configured to house the main sound-absorbing element 4, wherein one side of the shell forms a cup-like or concave-like outline. The outer edge 23 of the shell 2 may be connected to the outer edge 52 of the intermediate shell 5 with adhesive or other fixed solution which prevents the sound to pass through a crack between the shell 2 and the intermediate shell 5. The intermediate shell aperture 51 and an outer surface are parallel to the ear cushion 6 in such way that the ear cushion aperture 61 and the intermediate shell aperture 51 are aligned or almost aligned. The ear cushion 6 may be attached to the outer surface of the intermediate shell 5 with adhesive or other known attachment solutions. The intermediate shell 5 may additionally comprise a rim 26 extending from the ear cushion 6 and contacting inner surface of the shell 2 in a rigid connection between the intermediate shell 5 and the shell 2 for a better connectivity.

The shell aperture 21 may locate at the middle of the shell 2 and having edges that are turned inward the shell 2 in such way that the edges may form a second shaft 22, which has larger diameter than the shaft 12 of the switch 1, to receive the shaft 12 of the switch 1. The second shaft 22 may comprise a counterpart 23 to the guide 13 which can be matching threads on an inner surface of the second shaft 22, as illustrated in FIGS. 1-3. The guide 13 i.e. threads are located on the outer surface of the shaft 12 of the switch 1 contacting the counterpart 23 i.e. matching threads inside the shell aperture 21. The second shaft 22 can be shorter or equal length as the shaft 12 of the switch 1.

The shell 2 is free of ventilation holes 15 and is designed to bounce the sound away from the ear protection device and is made of acoustically inert or solid vibration-free material, for example. The attenuation level will suffer when the ventilation holes 15 are in the shell 2 and therefore, may not meet the EN352 standard.

The switch 1 is arranged to be rotatable between a first position and a second position. In the first position (FIG. 2), the ventilation holes 15 are exposed from the interior section of the shell 2 allowing air to flow inside and outside the interior space of the ear protection device. The term "exposed" in this context refers to being revealed and open to view or visible to the outside. In the second position (FIG. 3), the ventilation holes 15 are covered by the shell 2 and located inside the interior section of the shell 2 preventing the air to flow inside and outside the interior space.

Figure 4:
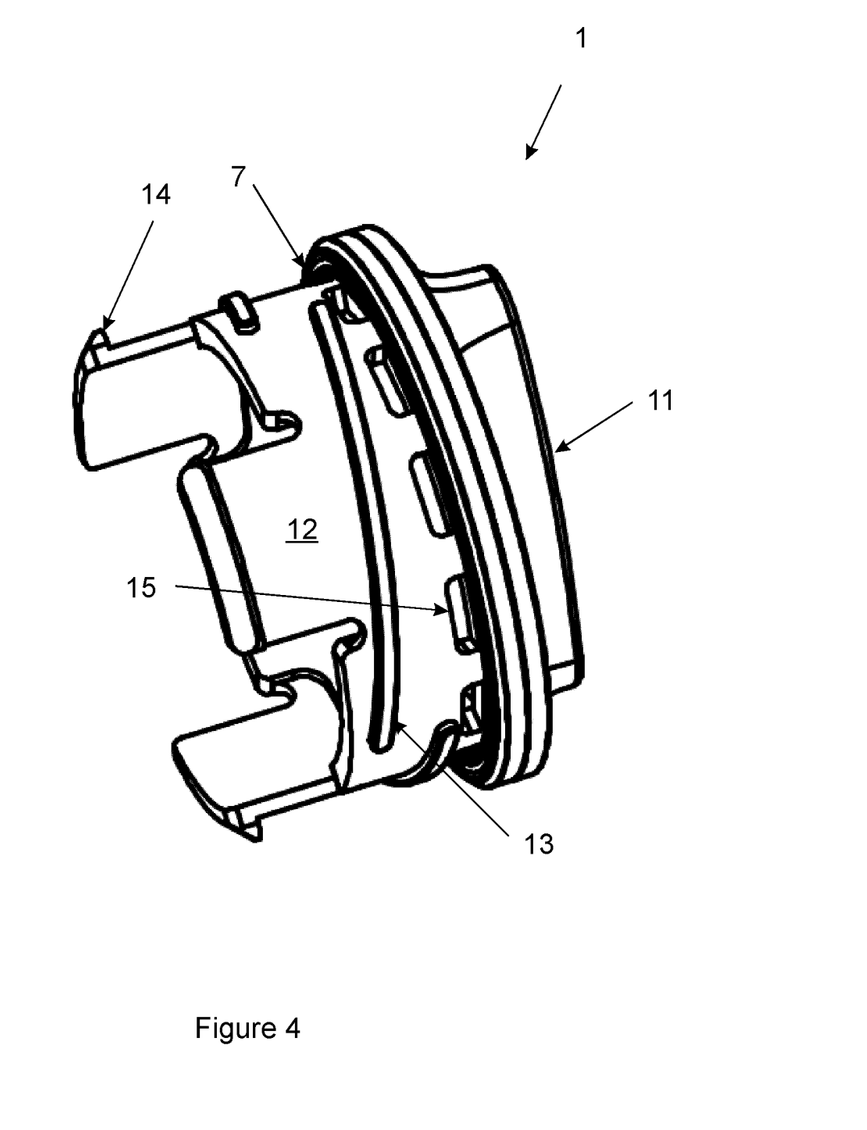
FIG. 4 illustrates a closer view of a switch of the ear protection device according to the first embodiment.

FIG. 4 illustrates a closer view of the switch of the ear protection device according to the first embodiment. The switch 1 further comprises a stopper 14 which can be connected to the shaft 12 or integrated in the shaft 12. The stopper 14 is arranged to prevent the rotation of the switch 1 when the switch 1 has reached the first position. As illustrated in FIGS. 2-4, the stopper 14 can be one or several longitudinal extensions of the shaft 12 with outward folded edges stopping the rotation of the shaft 12 when the end of the second shaft 22 contacts the folded edge preventing the rotation of the shaft 12. However, the stopper 14 may have other designs in other embodiments.

The shaft 12 may have a hollow inner section, which may define a cylindrical space for an additional sound-absorbing element 3. The additional sound-absorbing element 3 can be made of same material as the main sound-absorbing material 4.

The ventilation holes 15 can be arranged at a same transverse plane of a rotation axis A of the shaft 12, wherein a virtual line on the same transverse plane may pass through from one ventilation hole 15 to another. Practically, it means the ventilation holes 15 are arranged in such way that they are visible from the side view in the first position (FIG. 2) but not visible when viewed along the rotation axis A of the shaft 12. As illustrated in FIGS. 1-4, the ventilation holes 15 can be located around the shaft 12 of the switch 1 between the holder portion 11 and the guide 13. When the user rotates the switch 1 to the first position, the shaft 12 protrudes a predetermined distance from the ear cushion 6 and the ventilation holes 15 are located at said predetermined length and exposed.

The ventilation holes 15 can be circular, oval or quadrangle or mixture thereof, and they are arranged to exchange the air between the interior space and outside the ear protection device. The user's ears and skin radiate body heat which heats up the air in the interior space and may cause discomfort. When the ventilation holes 15 are exposed, they allow the cooler ambient air to replace the warm air inside the ear protection device. Additionally, when the ventilation holes 15 are arranged at same transverse plane of the shaft 12, it allows the air to ventilate faster inside the interior space when there are several inlets and outlets around the ear. When the ventilation holes 15 are spread around the ear, the user may also have better perception where the sound comes from.

A sealing ring 7 may be arranged between the ventilation holes 15 and the holder portion 11 of the switch 1 and contacting the shell 2 in the second position to prevent the air to pass through a crack between the switch 1 and the shell 2. When switching to the first position, the sealing ring 7 moves with the switch 1 away from the shell 2. The sealing ring 7 may be arranged to surround the whole circumference of the shaft 12.

The sealing ring 7 may locate behind the exterior surface of the switch 1. At the shell aperture 21, a step 24 may be formed between the second shaft 22 and the outer surface of the shell 2 to accommodate the sealing ring 7, wherein the sealing ring 7 is aligned with the transverse plane of the second shaft 22. In the second position, the sealing ring 7 may be completely covered by the shell 2 and the switch 1 to enhance the sealing. Additionally, in the second position, the ventilation holes 15 are covered by the shell 2 and sealed with the sealing ring 7, which results in improved attenuation.

The shell 2 may comprise two pins 25 on the outer surface of the shell 2 and located on both sides of the switch 1. The pins 25 are arranged to facilitate attaching a headband or an attachment piece to the ear protection device, wherein the headband connects two ear protection devices, and the attachment piece may attach the ear protection device to a safety helmet.

Figure 5:
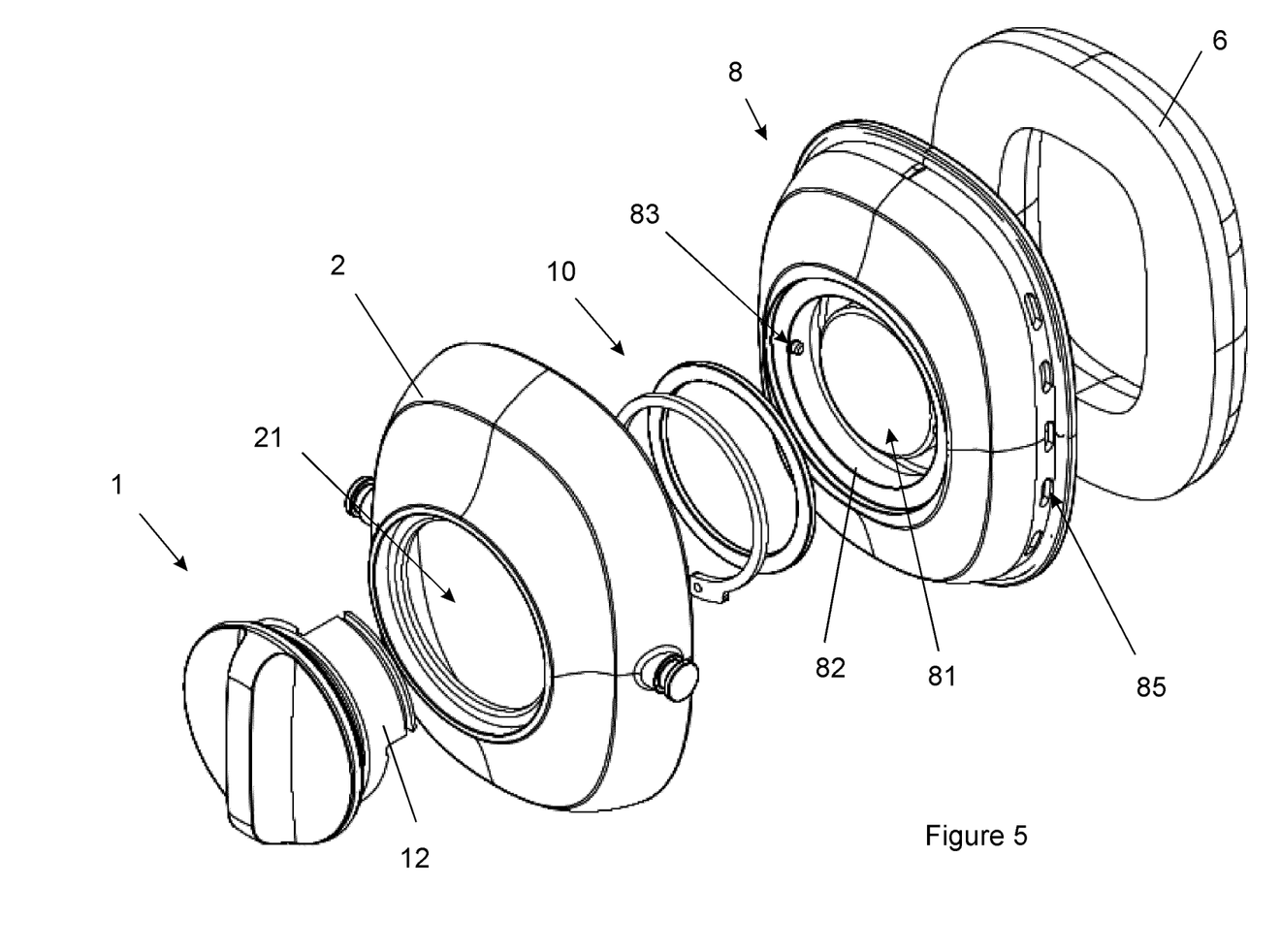
FIG. 5 illustrates an exploded view of an ear protection device according to a second embodiment.
Figure 6:
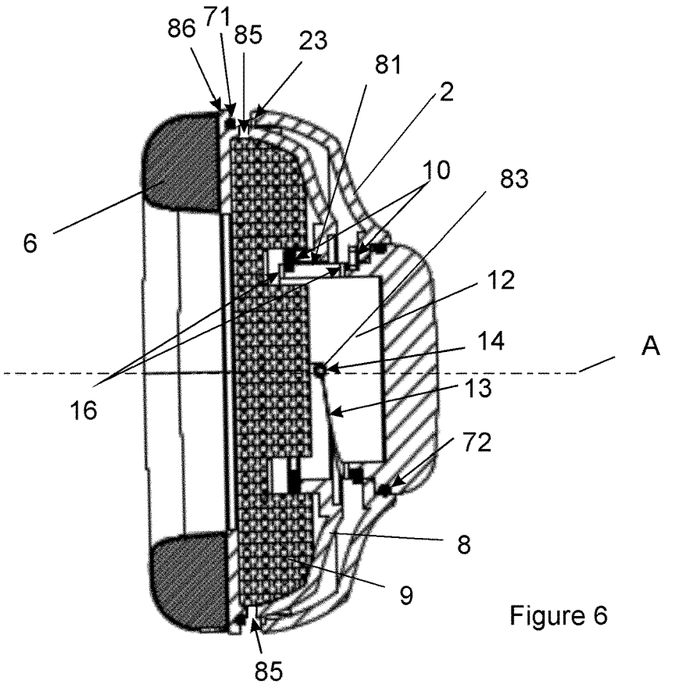
FIG. 6 illustrates a cross-sectional view of the ear protection device according to the second embodiment in the first position.
Figure 7:
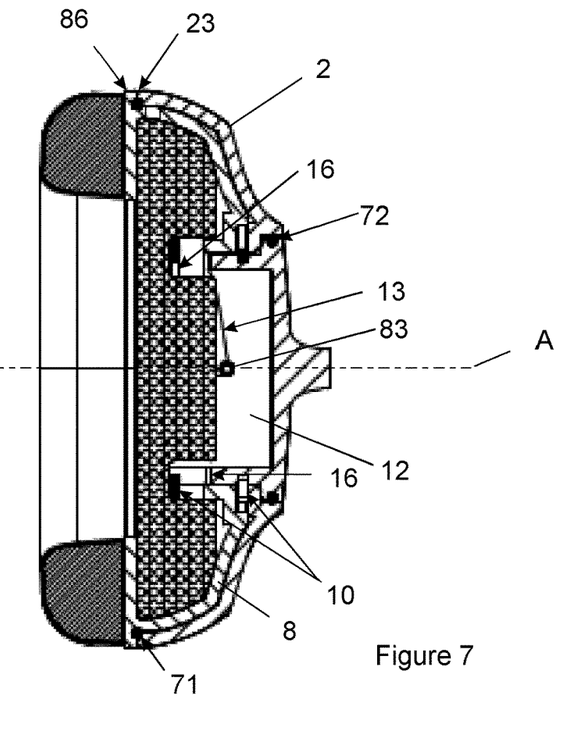
FIG. 7 illustrates a cross-sectional view of the ear protection device according to the second embodiment in the second position.
Figure 8:
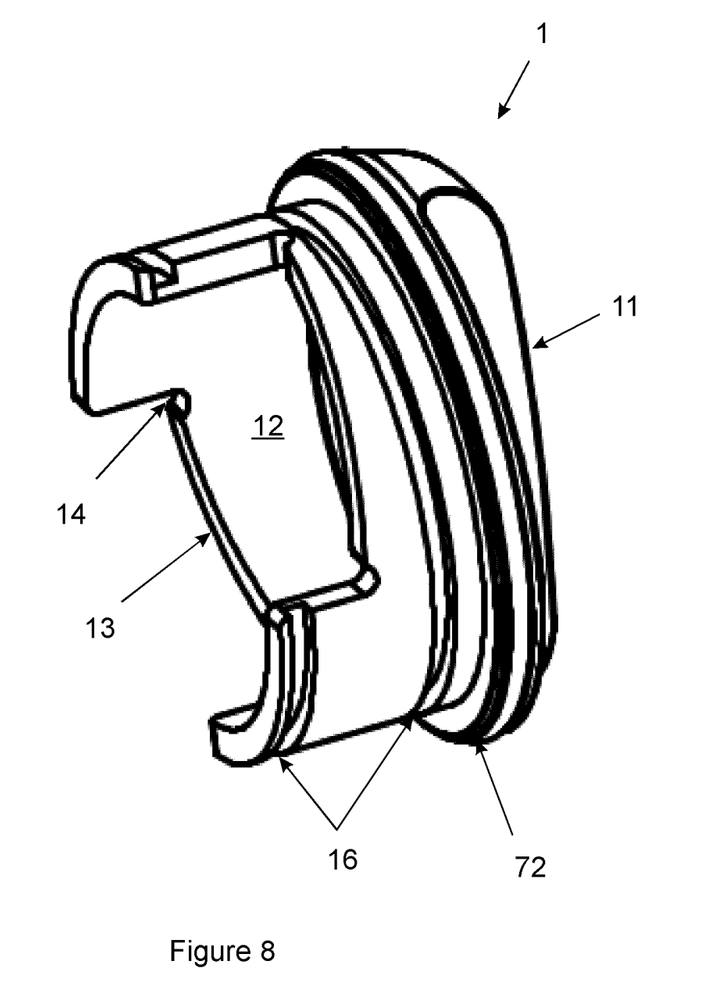
FIG. 8 illustrates a closer view of a switch of an ear protection device according to the second embodiment.

FIGS. 5-8 illustrate a second embodiment. FIG. 5 illustrates an exploded view of an ear protection device according to the second embodiment. FIG. 6 illustrates a cross-sectional view of the ear protection device according to the second embodiment in the first position. FIG. 7 illustrates a cross-sectional view of the ear protection device according to the second embodiment in the second position. FIG. 8 illustrates a closer view of the switch 1 of the ear protection device according to the second embodiment.

The embodiment of FIGS. 5-8 is very similar to the one explained in connection with FIGS. 1-4. Therefore, the embodiment of FIGS. 5-8 is in the following mainly explained by pointing out differences.

The second embodiment comprises a switch 1, a shell 2, an ear cushion 6 and additionally an inner shell 8. The inner shell 8 is arranged between the shell 2 and the ear cushion 6 and further connected to the shaft 12 of the switch 1. The inner shell 8 may be attached to the ear cushion 6 by an adhesive or other known attachment solutions. The inner surface of the inner shell 6 and the transverse plane of the end of the shaft 12 of the switch 1 may define a space for at least one sound-absorbing element 9.

When switched to the first position (FIG. 6), the shell 2 and the switch 1 move away from the ear cushion exposing ventilation holes 85 from the interior of the shell 2. The ventilation holes 85 in this embodiment are located at the inner shell 8 and arranged at the same transverse plane of the rotation axis A of the shaft 12 in such way that they are visible from the side view in the first position.

The inner shell 8 further comprises an inner shell aperture 81, in which the shaft 12 of the switch 1 is arranged to fit. The inner shell aperture 81 may locate at the middle of the inner shell 8 and having edges that are turned inward the inner shell 8 in such way that the edges may form an inner shell shaft 82, which has larger diameter than the shaft 12 of the switch 1, to receive the shaft 12 of the switch 1.

The inner shell shaft 82 may have substantially same diameter as the shell aperture 21. The inner shell shaft 82 may correspond and be aligned with the shell aperture 21 in such way that the shaft 12 of the switch 1 is connected to both shell 2 and inner shell 8 and rotatable within the apertures 21, 81. The shell 2 and the inner shell 8 may have similar cup-like or concave-like shape. When the switch 1 is turned to the second position, the outer surface of the inner shell 8 corresponds and contacts with the inner surface of the shell 2 so that the shell 2 covers the ventilation holes 85 of the inner shell 8.

The guide 13 of the shaft 12 in this embodiment is shown as an inclined step but threads or other designs can also be implemented. Corresponding counterpart 83 in this embodiment may be a protrusion extending from the inner shell aperture 81. When the switch 1 is turned between the first and second position, the protrusion is arranged to slide against the inclined step resulting the shaft 12 to move the predetermined distance, which is determined by the inclination of said inclined step, from the ear cushion 6. The stopper 14 may be an inner corner of the inclined step which prevents the switch 1 to turn past the first position. However, other designs may be applicable.

The second embodiment may also comprise additional switch holders 10 to attach the switch 1 within the shell 2 and the inner shell 8. The switch holders 10 may be two rings surrounding at least partially the circumference of the shaft 12 and fixedly attached to the inner shell aperture 81 and the shell aperture 21, respectively. The switch holder 10 prevents the switch 1 to separate from the apertures 21, 81 by contacting a projection or depression 16 around the circumference of the shaft 12 on the outer surface of the shaft 12 while allowing the shaft 12 to rotate in relation to the shell 2. The switch holders 10 may be manufactured of plastic or rubber such as a sealant. In some embodiments, the switch holder 10 may be a spring washer to provide a vibration resistant function.

A sealing ring 71 may be arranged around the inner shell 8 and next to the ventilation holes 85. When switching to the first position the sealing ring 71 is revealed with the ventilation holes 85. The sealing ring 71 is arranged to surround the whole circumference of the inner shell 8. An inner shell flange 86 protruding from the outer surface of the inner shell 8 and parallel to the ear cushion 6 may be arranged between the sealing ring 71 and the ear cushion 6 to enhance the sealing. When the switch 1 is turned to the second position, the sealing ring 71 may be completely covered by the outer edge 23 of the shell 2 and the inner shell flange 86, thus preventing air to pass through a crack between the inner shell 8 and the shell 2.

The second embodiment may further comprise a second sealing ring 72 surrounding the switch 1 and contacting the shell aperture 21 to prevent the air to pass through a crack between the switch 1 and the shell 2, wherein the switch 1 is rotatable in relation to the shell 2, the inner shell 8 and the ear cushion 6.

The aim of the present invention is to provide an effective ear protection device which meets the EN352 standard, and having a switch, which allows the user to ventilate inside the ear protection device to provide comfort to the user's ear area and to turn the attenuation off without taking the ear protection device off.

What is claimed is:

1. An ear protection device, comprising:
   an ear cushion for contacting around an ear to seal off an interior space of the ear protection device from surroundings,
   a switch comprising a holder portion and a shaft with a guide,
   a shell comprising an interior section and a shell aperture wherein edges of the shell aperture engage with the guide of the switch, and said shell is provided between the ear cushion and the switch,
   the switch is rotatable between a first position and a second position, wherein in the first position, ventilation holes are exposed from the interior section of the shell allowing air to flow inside the interior space,
   and in the second position, the ventilation holes are covered inside the interior section of shell and directly covered by the shell, preventing the air to flow inside the interior space and,
   a sealing ring next to the ventilation holes and said sealing ring contacts the shell in the second position.

2. The ear protection device according to claim 1, wherein the shaft comprises a stopper for preventing the rotation of the switch past a predetermined distance from the ear cushion.

3. The ear protection device according to claim 1, wherein the ventilation holes are arranged at a same transverse plane of a rotation axis of the shaft.

4. The ear protection device according to claim 1, wherein the guide is threads on outer surface of the shaft of the switch contacting a counterpart on the shell aperture.

5. The ear protection device according to claim 4, wherein the ventilation holes are arranged around the shaft between the sealing ring and the threads.

6. The ear protection device according to claim 1, wherein the ear protection device further comprises an intermediate shell provided between the shell and the ear cushion, wherein the inner surface of the shell and the inner surface of the intermediate shell and optionally the outer surface of the shaft of the switch defines a space for a main sound-absorbing element.

7. The ear protection device according to claim 6, wherein an inner section of the shaft of the switch is hollow and defines a space for an additional sound-absorbing element.

8. The ear protection device according to claim 1, wherein the ear protection device further comprises an inner shell comprising an inner shell aperture and a counterpart.

9. The ear protection device according to claim 8, wherein the counterpart is a protrusion extending from the inner shell aperture, and the guide of the shaft is an inclined step contacting said protrusion.

10. The ear protection device according to claim 8, wherein the inner surface of the inner shell and the transverse plane of the end of the shaft of the switch defines a space for a sound-absorbing element.

11. The ear protection device according to claim 8, wherein the ventilation holes are arranged at the inner shell and the sealing ring surrounds the inner shell.

12. The ear protection device according to claim 8 wherein the ear protection device further comprises a second sealing ring surrounding the switch and contacting the shell aperture.

13. The ear protection device according to claim 8, wherein the ear protection device further comprises at least one switch holder surrounding at least partially the circumference of the shaft of the switch and configured to prevent the switch to separate from the shell aperture and inner shell aperture.

14. The ear protection device according to claim 1, wherein the shell is free of ventilation holes.

15. An ear protection device, comprising:
- an ear cushion for contacting around an ear to seal off an interior space of the ear protection device from surroundings,
- a switch comprising a holder portion and a shaft with a guide,
- a shell comprising an interior section and a shell aperture wherein edges of the shell aperture engage with the guide of the switch, and said shell is provided between the ear cushion and the switch,
- the switch is rotatable between a first position and a second position, wherein in the first position, ventilation holes are exposed from the interior section of the shell allowing air to flow inside the interior space,
- and in the second position, the ventilation holes are covered inside the interior section of shell and directly covered by the shell, preventing the air to flow inside the interior space,
- an inner shell comprising an inner shell aperture and a counterpart, and
- wherein the ventilation holes are arranged at the inner shell and a sealing ring surrounds the inner shell.

16. The ear protection device according to claim 15, wherein the shaft comprises a stopper for preventing the rotation of the switch past a predetermined distance from the ear cushion.

17. The ear protection device according to claim 15, wherein the ventilation holes are arranged at a same transverse plane of a rotation axis of the shaft.

18. The ear protection device according to claim 15, wherein the guide comprises threads on an outer surface of the shaft of the switch contacting the counterpart on the shell aperture.

19. The ear protection device according to claim 15 wherein the ear protection device further comprises a second sealing ring surrounding the switch and contacting the shell aperture.

20. The ear protection device according to claim 15, wherein the ear protection device further comprises at least one switch holder surrounding at least partially the circumference of the shaft of the switch and configured to prevent the switch to separate from the shell aperture and inner shell aperture.

* * * * *